US007439057B2

(12) United States Patent(10) Patent No.: US 7,439,057 B2
Frangos et al.(45) Date of Patent: Oct. 21, 2008

(54) CONVECTIVE FLOW TISSUE ASSEMBLY

(75) Inventors: John A. Frangos, La Jolla, CA (US);
Peter Sobolewski, San Diego, CA (US)

(73) Assignee: La Jolla Bioengineering Institute, La Jolla, CA (US)

( * ) Notice: Subject to any disclaimer, the term of this patent is extended or adjusted under 35 U.S.C. 154(b) by 602 days.

(21) Appl. No.: 10/991,079

(22) Filed: Nov. 16, 2004

(65) Prior Publication Data

US 2006/0105452 A1    May 18, 2006

(51) Int. Cl.
 C12M 1/14    (2006.01)
 C12N 5/08    (2006.01)
 A61F 2/00    (2006.01)
(52) U.S. Cl. ............... 435/299.1; 435/395; 424/423
(58) Field of Classification Search ............ 435/299.1, 435/395; 424/423
 See application file for complete search history.

(56) References Cited

U.S. PATENT DOCUMENTS

| | | | | | |
|---|---|---|---|---|---|
| 5,512,475 | A | * | 4/1996 | Naughton et al. ............ 424/484 |
| 5,792,603 | A | * | 8/1998 | Dunkelman et al. ........... 435/1.2 |
| 6,306,424 | B1 | * | 10/2001 | Vyakarnam et al. .......... 424/426 |
| 6,503,273 | B1 | * | 1/2003 | McAllister et al. .......... 623/1.41 |
| 6,592,623 | B1 | * | 7/2003 | Bowlin et al. ............ 623/14.13 |
| 6,596,274 | B1 | * | 7/2003 | Abatangelo et al. ......... 424/93.7 |
| 7,179,287 | B2 | * | 2/2007 | Wolfinbarger, Jr. ......... 623/1.41 |
| 2002/0131989 | A1 | * | 9/2002 | Brown et al. ................. 424/428 |
| 2003/0138950 | A1 | * | 7/2003 | McAllister et al. ........... 435/366 |
| 2004/0126405 | A1 | * | 7/2004 | Sahatjian et al. ............. 424/423 |

OTHER PUBLICATIONS

Barron V., Lynos E., Stenson-Cox C., McHugh P.E., and Pandit A. Bioreactors for Cardiovascular Cell and Tissue Growth: A Review. 2003. Annals of Biomedical Engineering, vol. 31, pp. 1017-1030.*
Stegemann J. P. and Nerem R. m. Phenotype Modulation in Vascular Tissue Engineering using biochemical and Mechanical Stimulation. 2003.Annals of Biomedical Engineering, vol. 31, pp. 391-402.*

* cited by examiner

Primary Examiner—Walter D Griffin
Assistant Examiner—Lydia Edwards
(74) Attorney, Agent, or Firm—O'Melveny & Myers LLP

(57) ABSTRACT

The present invention provides for an improved in vitro tissue assembly system and related methods that includes and uses a bioreactor, a porous mandrel disposed in the bioreactor, and components that provide for the circulation of culture media and cell suspensions within the bioreactor and through the porous mandrel. The circulation of the culture media and cell suspensions within the bioreactor produces a radial, convective flow and drag forces that result in the deposition of cells on the mandrel to form a tissue construct. Upon completion of the culture and tissue formation process, the tissue construct may be removed from the mandrel for subsequent in vivo use.

18 Claims, 3 Drawing Sheets

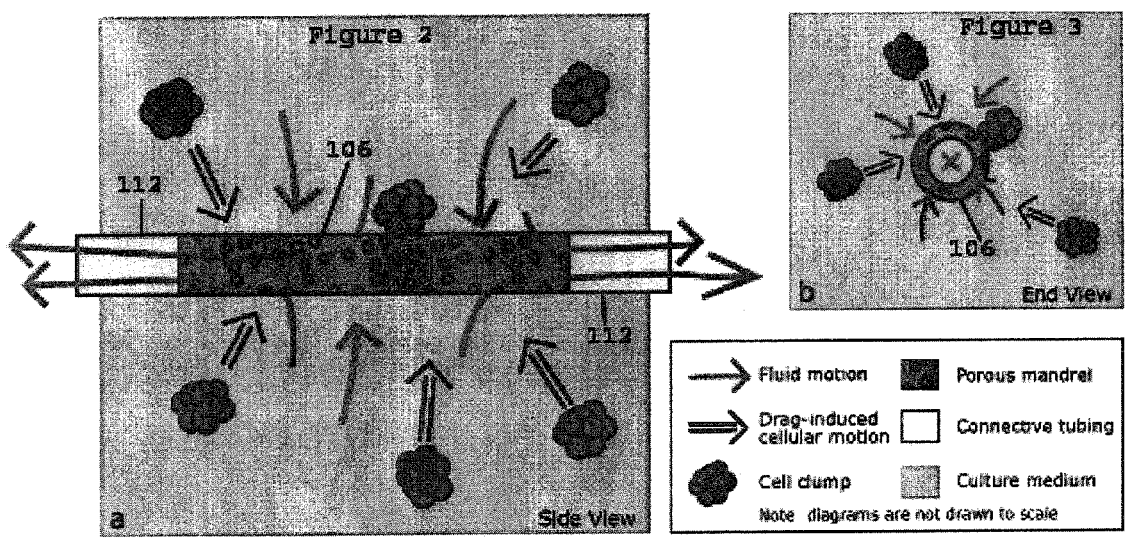

CONVECTIVE FLOW TISSUE ASSEMBLY

GOVERNMENT INTERESTS

This invention was made with government support under HL74587 awarded by the National Institute of Health. The government has certain rights in the invention.

FIELD OF THE INVENTION

The present invention relates to systems and methods for producing tissue constructs in vitro.

BACKGROUND

Heart disease is the leading cause of death in the United States, affecting 12 million Americans and with an annual economic burden that exceeds 110 billion dollars. Coronary heart disease accounts for the largest portion of heart disease cases. Presently, coronary artery bypass graft ("CABG") is an accepted approach both on an elective and emergency basis for restoring blood flow to areas of the heart affected by coronary artery stenosis. CABG is one of the most common medical procedures with more than 600,000 conducted annually.

Clinically, in a CABG procedure the stenotic coronary artery is bypassed using a graft consisting of a saphenous vein or a mammary artery conduit. Unfortunately, not only is graft harvesting invasive but patients frequently lack adequate autogenous vessels to serve as bypass conduits, particularly in the case of patients who require repeated, multiple bypass procedures. Recognition of this problem led to the development of the first tissue engineering efforts almost 30 years ago. For example, Bregman and Wolinsky used subcutaneously implanted pulsed balloons to produce an autologous graft conduit via encapsulation. While their results were mixed, the concept of a tissue engineered vascular graft ("TEVG") was established. Rather than using artificial materials, the tissue engineering approach seeks to replace pathological tissue with new tissue engineered specifically for the patient.

Twelve years later, Weinberg and Bell introduced in vitro assembly to the field by combining collagen gels with living vascular cells. Unfortunately, their grafts displayed burst strengths of less than 10 mm Hg and even the use of DACRON sleeves did not increase the burst strength of the grafts beyond 350 mm Hg. While these vessels acted as permeability barriers, the poor mechanical properties and the requirement of artificial materials limited this approach. Since the initial work by Weinberg and Bell, there have been various attempts at obtaining improved mechanical properties from completely biological, collagen gel based TEVGs. Unfortunately, the maximum demonstrated burst strength of these engineered tissues has been only 225 mm Hg, which is much lower than the 1700 mm Hg burst strength of human saphenous veins. Thus, it does not seem likely that this approach will see successful clinical application.

Other approaches have also been developed, but these approaches also have various disadvantages and insufficiencies. L'Heureux and coworkers were able to produce completely biological TEVGs by manually wrapping sheets of smooth muscle cells ("SMC") and fibroblasts around a mandrel. Following eight weeks of culture, the mandrel was removed and endothelial cells ("EC") were seeded on the luminal side of the graft. In vitro mechanical testing of the TEVGs showed a mean burst strength of 2594 mm Hg and histological analysis demonstrated the presence of elastin. Unfortunately, the in vivo animal study showed mixed results. The TEVGs showed "tissue-like" suturability and handling characteristics, but seven day patency was just 50%. Furthermore, problems with delamination of the layers and transport insufficiency have been observed. Finally, this approach utilized neonatal cells and the labor-intensive methodology required to use neonatal cells is impractical for large scale production of TEVGs having consistent biological and mechanical properties.

Niklason and coworkers utilized a different approach for producing TEVGs in vitro. Niklason used a tube of treated biodegradable polygalactic acid ("PGA") polymer mesh as structural support for seeded SMCs. The tube was fitted inside a bioreactor and subjected to luminal pulsed conditions of 165 bpm, mimicking those of the fetus while in culture, for eight weeks prior to the lumen being seeded with ECs. The vessels showed some response to pharmacological agents, including serotonin, endothelin-1, and prostaglandin $F_2a$, and demonstrated good mechanical properties including a mean burst strength above 2000 mm Hg. Histologically, the vessels exhibited collagen production, an endothelial cell layer that stained positively for von Willebrand factor and PECAM-1 (CD31), a layer of SMCs that expressed SM α-actin, heavy chain myosin, and calponin, and trace non-degraded polymer fragments. Finally, a four week in vivo study showed 100% patency for two implanted, pulsed TEVGs. While the initial results were very promising for tissues engineered with this technique, these TEVGs were not 100% biological and the degradation of the PGA mesh appeared to affect the SMCs, dedifferentiating them, perhaps due to the local hyperacid conditions. Furthermore, the culture conditions, while biomimetic, only resulted in wall shear stresses of 0.1 dyne/$cm^2$ to 0.3 dyne/$cm^2$, as compared to the physiological wall shear stress of approximately 10 dyne/$cm^2$.

Campbell and coworkers used a methodology similar to that of Bregman and Wolinsky. Campbell implanted silastic tubing into the peritoneal cavity of rats and rabbits. Following harvesting after two weeks, the tubing was removed and the encapsulation layer was inverted. The resulting vessel consisted of three layers: an inner mesothelial layer that stained positively for von Willebrand factor; a middle myofibroblast layer that stained positively for α-SM actin, desmin, and heavy chain myosin; and an outer connective tissue layer, as well collagen matrix between cells. Furthermore, the TEVGs demonstrated response to pharmacological agents such as KCl, acetylcholine, and phenylephrine. The magnitude of the response to pharmacological agents was, however, much lower than that of native arteries. Overall patency rate was 67% over periods of two, three, and four months of in vivo grafting. Unfortunately, the mechanical properties of the vessels were not characterized. In addition, the cell types present in the vessel were not the same as those in native vessels. Furthermore, the assembly methodology was invasive and relied on the silastic mandrel producing a strong foreign body inflammatory response. As such, this method is not well suited for producing grafts for sick patients and is not likely to see approval by the US Food and Drug Administration for wide spread clinical use.

It is quite clear that despite their scientific value, all of the previous studies described above and known in the art have limitations regarding their ability to achieve clinical efficacy and practical application for disease management. Accordingly, there is a long felt but unmet need for improved systems and methods for in vitro generation of tissue constructs and grafts.

There is also a long felt but unmet need for methods for in vitro generation of tissue constructs and grafts that provide for tissue with high burst strengths, high patency, and other biological and mechanical properties that are consistent with in vivo use.

Additional features and objects of the invention will become apparent from the following description in which the preferred embodiments are set forth in detail in conjunction with the accompanying drawings.

SUMMARY OF THE INVENTION

The present invention provides for an entirely novel approach to in vitro tissue generation called convective flow tissue assembly ("CFTA"). This novel approach to generating tissues, including, e.g., TEVGs, involves assembling cells on an inert, porous mandrel via drag forces produced by a radial, convective flow of culture medium. The mandrel only serves as a template and the tissue construct is ultimately removed from the mandrel.

The present invention addresses the shortcomings of previous in vitro tissue generation efforts. The present invention provides for tissue constructs that are completely biological and have accurate tissue morphology. For TEVGs, for example, the tissue constructs have the three-layer morphology of native arteries approximating the intima, media, and adventitia, while avoiding delamination and uniformity issues. Since the mandrel is inert and only serves as a temporary tubular template, no polymer will remain in the tissue construct nor will there be adverse effects of any polymer breakdown products. The culture conditions can be adjusted to mimic those experienced by cells in vivo and results in maintenance of differentiated phenotype and adequate mechanical properties, due to extracellular matrix ("ECM") production.

Furthermore, the transmural flow used by the present invention to generate tissue provides adequate transport of nutrients and oxygen to all parts of the tissue construct. Equally important, since the tissue assembly may be accomplished wholly in vitro by the convective flow in a bioreactor and from adult, autologous cells, the present invention is practical for both FDA approval and wide-scale commercial and economic viability. This last characteristic is of particular importance because in order for any tissue production methodology to make a clinical impact it must be readily available. The present invention is readily automated and scalable and, as a result, should translate well to the manufacturing setting. Thus, the novel tissue assembly methodology provided by the present invention fulfills all of the criteria needed to achieve optimal and effective tissue constructs and in vitro tissue production.

BRIEF DESCRIPTION OF THE FIGURES

FIG. 2 illustrates a convective flow tissue assembly process of the present invention.

FIG. 3 illustrates an end view of a mandrel during a convective flow tissue assembly process of the present invention.

DETAILED DESCRIPTION

Figure 1:
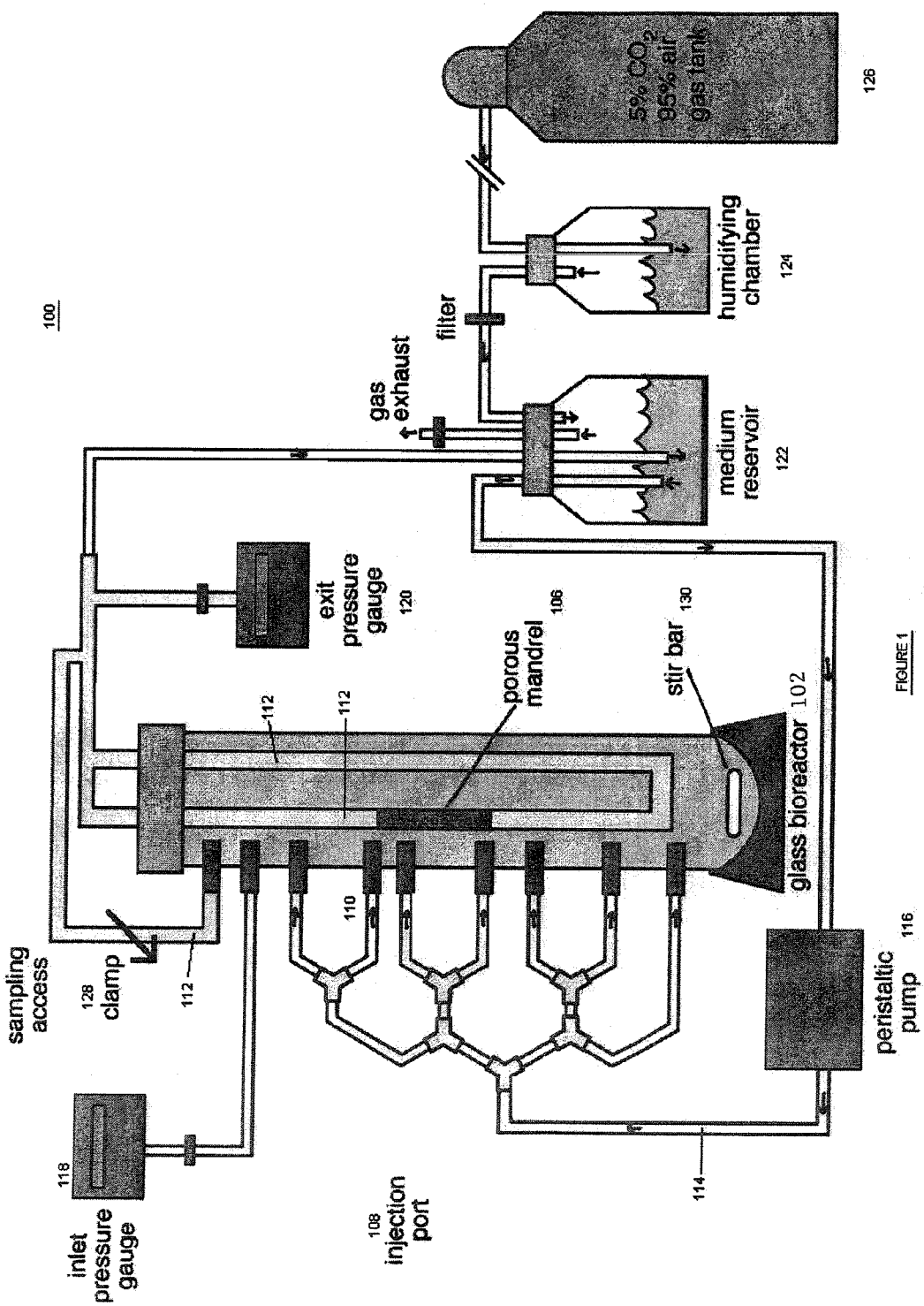
FIG. 1 illustrates a convective flow tissue assembly system of the present invention.

The present invention provides for novel systems and methods for performing convective flow tissue assembly and producing tissue constructs in vitro. The processes of the present invention generally involve the assembling of cells on an inert, porous mandrel, which only serves as a template and will ultimately be removed, via drag forces produced by a radial, convective flow of culture medium. The convective flow may be maintained by holding the luminal side of the mandrel at a lower pressure than that of the main bioreactor chamber, resulting in a transmural pressure gradient and radial flow within the bioreactor. As a result, cells may be actively deposited on the mandrel by fluid drag forces, thereby maximizing efficiency and ensuring a uniform distribution of cells on the mandrel. The pressure gradient will be radially symmetric and will result in fluid flow, which will also be symmetric in the radial direction.

The CFTA cell deposition system of the present invention is self correcting. For example, any irregularity in the cell deposition will locally alter the hydraulic resistance of the mandrel, which will result in an inverse effect on the fluid flow that, in turn, drives the cell deposition. For example, local over-deposition will locally increase the hydraulic resistance at that portion of the mandrel and will serve to divert fluid flow, thereby increasing the deposition of cells on the rest of the mandrel. Finally, stirring may be implemented at the bottom of the bioreactor to minimize the effects of gravity-driven sedimentation. Consequently, in terms of the uniformity of the resultant vascular grafts, this methodology is far superior to the prior art pipetting or rolling methodologies.

It is also important to note that with the present invention tissue construct thickness does not rely solely on initial cell proliferation since additional cell seedings, which will also take advantage of the self-correcting mechanism of the processes of the present invention, can occur during the culture process. Furthermore, when using the present invention the cells are not seeded in the traditional tissue engineering sense of the word. That is, the cells will not attach to the mandrel, but instead will be held in place by the pressure-driven flow, allowing the cells to secrete extracellular matrix and form a tissue. The mandrel only acts as a mechanical support and three-dimensional template to define the shape of the formed tissue, and will be removed once sufficient or desired tissue thickness is achieved. Layered constructs may be achieved by periodically injecting different cell types, such as, e.g., smooth muscle cells, fibroblasts, and the like, into the culture.

The assembly process of the present invention is not specific to any particular tissue engineered tissue or organ. Rather, the process lends itself well to the assembly of any multi-layered vascularized organ, such as, e.g., vascular grafts, trachea, esophagus, liver, and the like. Sheets of tissue, such as, e.g., tissue engineered skin, skeletal muscle, cardiac muscle, and the like, may also be assembled by slicing open a cylindrical construct made using the present invention. Furthermore, since construct thickness is not solely dependent on initial cell proliferation and additional seedings can be conducted, almost any cell type can be used. In particular, both proliferative cell lines, such as, e.g., stem cells, cell-culture lines, and the like, as well as adult, autologous cells from the patient can be used.

Turning to FIG. 1, a convective flow tissue assembly system 100 of the present invention is illustrated. The system 100 includes a bioreactor 102 that preferably includes a transparent housing or chamber having an interior volume. The bioreactor 102 contains the CFTA process and may be manufactured from a substantially transparent material such as, e.g., glass, quartz, clear polymers such as acrylic, and the like. The bioreactor 102 may be sterilized by suitable processes such as autoclaving, EtO, or Sterrad. Preferably, the bioreactor 102 will be able to withstand at least 10 psi of pressure without exhibiting any substantial leaks or failures. The bioreactor 102 may include a large, scalable opening 104 for insertion and extraction of a mandrel 106, as well as inlets 110 for sterile injections of cell suspensions or sterile culture media exchange into the bioreactor 102, or for sampling from the bioreactor 102. If the system 100 includes a plurality of inlets 110, an injection port 108 upstream of the inlets 110 may be provided. When the system 100 includes a plurality of inlets 110, it may be more efficient to inject the cell suspensions upstream of the individual inlets 110 via the injection port 108 such that all of the inlets 110 are used to disperse the cells. The bioreactor 102 may include outlets or outlet ports 112 through which media flows and circulates through the bioreactor 102. In an alternative embodiment, a bioreactor includes either inlets 110 or injection ports 108 but not both.

Referring again to FIG. 1, culture media may be infused into the interior volume of the bioreactor 102 via the inlets 110 and, when present, injection port 108, and may be aspirated out of the interior volume of the bioreactor 102 via the outlets 112. As a result of the circulation of media through the bioreactor 102 via the inlets 110, injection port 108, and outlets 112, the radial flow profile required for CFTA is established. A magnetic stir bar 130 may optionally be used to minimize sedimentation in the bioreactor 102. For example, when used the magnetic stir bar 130 may be activated in order to circulate the culture media and the cell suspensions within the interior volume of the bioreactor 102, thereby minimizing sedimentation of the cells. The bioreactor 102 interior volume may range from 100 to 1000 ml.

As noted, the flow system 100 maintains the radial flow conditions required for CFTA. Preferably, sterilizable tubing 114, which may be formed from TEFLON, PHARMED, TYGON, or the like, is used to connect the bioreactor 102 to a pump 116. The pump may be a peristaltic, multichannel peristaltic, or other type of recirculating pump. The system 100 may also include two pressure gauges, an inlet pressure gauge 118 and an exit pressure gauge 120, that are used to monitor the pressure drop across the mandrel 106 during the CFTA process.

The system 100 may incorporate a medium reservoir 122 and a humidifying chamber 124 to assist in the tissue formation process and the maintenance of the radial flow conditions need for CFTA. For example, the culture media used in the system may be exposed to a gas mixture containing approximately 5% $CO_2$. In this embodiment, the gas mixture may be bubbled through water within the humidifying chamber 124, and subsequently introduced into the bioreactor 102 in order to maintain desired levels of humidity and pH within the bioreactor 102. In one embodiment, a gas tank 126 is provided and is used to contain a mixture of 5% $CO_2$ and 95% $O_2$ to which the culture media is exposed. Additionally, the medium reservoir 122 may be used to contain culture media that will be infused into the bioreactor 102 or that has been aspirated from the bioreactor 102. The gas mixture may also be introduced to the culture media within the medium reservoir 122. In an alternative embodiment, the flow system 100 includes several bioreactors 102 operating in parallel.

The system 100 includes a mandrel 106 that may be cylindrical in shape and is placed into the interior volume of the chamber of the bioreactor 102. The mandrel 106 serves as a support and template for the CFTA process. The mandrel 106 is preferably hollow and has an interior volume, and is rigid such that it maintains its shape throughout the process. In one embodiment, the mandrel 106 is an elongate tubular member with each end of the tubular member in communication with the outlets 112, as illustrated in FIG. 2. Here, the interior volume of the mandrel 106 is in fluid communication with the outlets 112.

The mandrel 106 is preferably porous to allow for fluid flow through its surface and interior volume, but the mandrel 106 must also minimize the in-growth of cells into the mandrel 106. To minimize in-growth or cell penetration while at the same time presenting a minimal resistance to transmural flow through the mandrel 106, the surface of the mandrel 106 preferably has pore sizes that range between 5 and 30 µm. Further, the mandrel 106 may be composed of a non-stick polymer that is inert and easily sterilizable, such as, e.g., polyethylene, PTFE, ePTFE, and the like. In one embodiment, the outer diameter of the mandrel 106 may range from 2 to 10 mm, while the inner diameter of the mandrel 106 may range from 1 to 9 mm.

Figure 4:
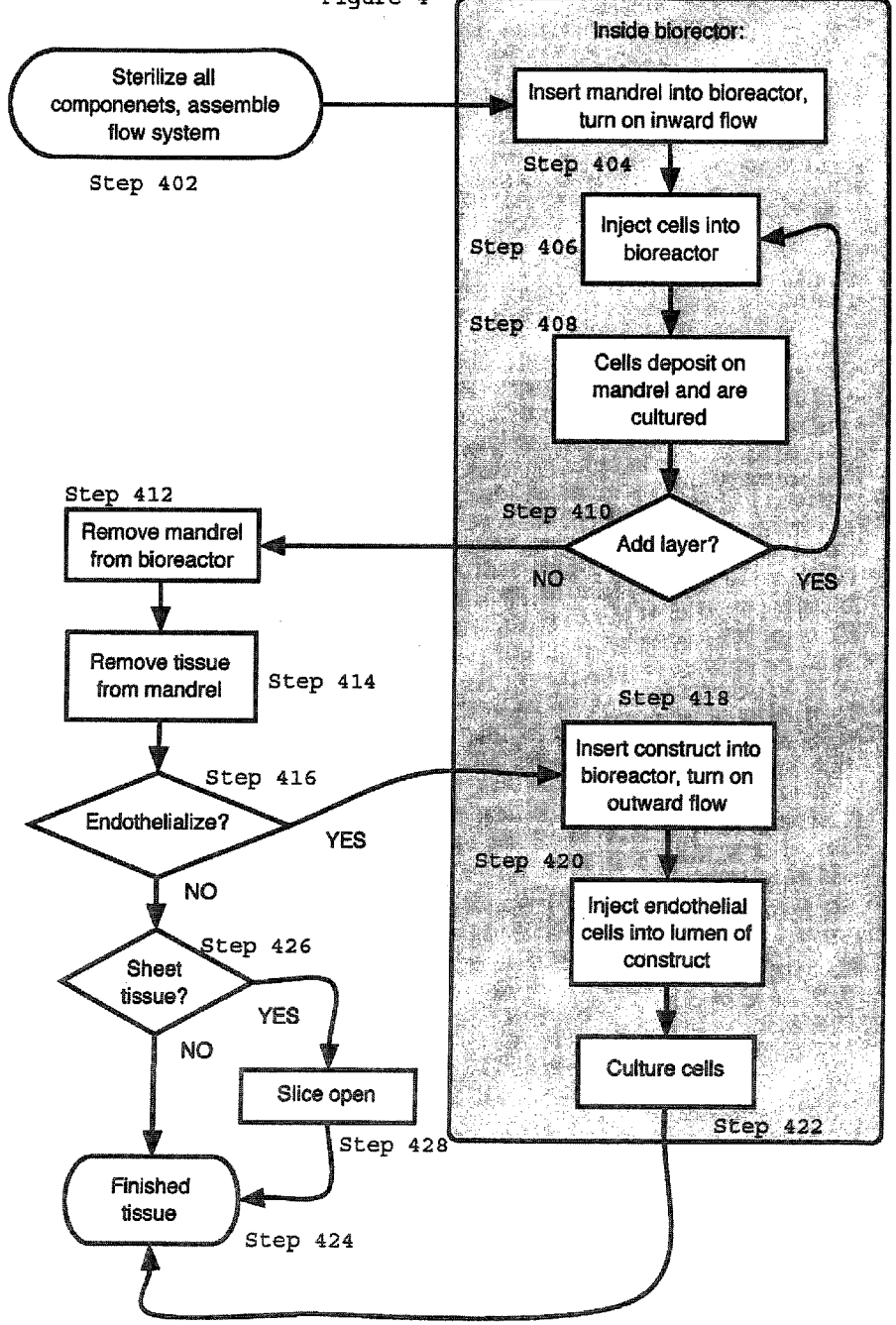
FIG. 4 is a flow chart that details a convective flow tissue assembly process of the present invention.

Referring now to FIG. 4, one process for using the system 100 is described. To operate the system 100, the bioreactor 102, mandrel 106, and all of the tubing and other components of the system 100 are sterilized and then assembled in a sterile environment. (Step 402). The mandrel 106 is then inserted into the bioreactor 102. (Step 404). With further respect to Step 404, the bioreactor 102 and media reservoir 122 are filled with sterile culture media and placed in a temperature controlled environment. The sterile culture media will be of a type appropriate for the culture of the selected cell type(s) for a particular reaction. Additionally, the culture media may be supplemented with suitable growth factors depending on the types of cells used for a particular reaction. The system 100 is then activated, including the gas tank 126 being turned on. The culture media is pumped into the bioreactor 102 by the pump 116. The culture media will circulate in the bioreactor 102 by the culture media flow entering the bioreactor 102 via the inlets 110 and injection port 108 (when included with the system 100) and then exiting the bioreactor 102 via the outlets 112. The outlets 112 are connected to the lumen of the mandrel 106. The outlets 112 may be connected at either end of the mandrel 106 or at both ends of the mandrel 106, as illustrated in FIGS. 1 and 2. In one embodiment, a magnetic stir plate and stir bar 130 is used with the system 100 to stir the culture media.

In addition to referring to FIG. 4, reference will also be made to FIG. 2, which is an isolated side view of the mandrel 106 within the bioreactor 102, and FIG. 3, which is an end view of the mandrel 106 during the convective flow tissue assembly process. A suspension of cells may be injected directly into the bioreactor 102 or upstream of the bioreactor 102 using inlets 110 and injection port 108. (Step 406). Fluid drag will direct the cells to the mandrel 106 and the pressure gradient will hold the cells against the mandrel 106. (Step 408). During the process of the present invention, the radial flow generated by the pressure gradient within the bioreactor 102 results in cellular assembly on the porous mandrel 106 via the deposition of deposit cells on the mandrel 106. For example, the luminal side of the mandrel 106 is preferably maintained at a lower pressure than the main chamber of the bioreactor 102, resulting in a transmural pressure gradient and an inward, radial flow. That is, the culture media within the bioreactor 102 will pass from the interior volume of the bioreactor 102 through the pores of the mandrel 106 and into the lumen of the mandrel 106. Due to fluid drag forces, cells carried in the culture media will be drawn to the surface of the mandrel 106 and be deposited and held on the surface of the mandrel 106 as a result of the radial flow in the bioreactor 102. Because the porosity of the mandrel 106 is preferably less than the size of the cells and the mandrel 106 is preferably inert, cells will typically not penetrate nor adhere, but will instead be held in place on the surface of the mandrel 106 by the radial flow resulting from the transmural pressure gradient. As a result of being deposited on the mandrel 106, the cells are assembled into tissue constructs. Furthermore, the mandrel 106 serves only as a three dimensional template and will not be incorporated into the tissue, and the tissue is formed in the shape of the mandrel 106.

Flocculants, including polyelectrolytes such as high molecular weight (ex. $2 \times 10^6$ Da) DEXTRAN, may be introduced into the bioreactor 102 in order to increase clumping of cells and thereby increasing drag. The flocculants reduce the electrostatic repulsion between cells, and as a result allow van der Waals forces to promote cell clumping. Because flocculation or clumping of cells has the effect of increasing hydrodynamic drag, flocculation will typically be used when fluid flow is too low to otherwise promote deposition of single cells onto the mandrel 106.

Cells will be maintained in culture and allowed to proliferate and/or additional injections of cell suspension may be administered until a desired construct thickness is achieved, such as, e.g., 3 mm for a TEVG. Once a cell layer has formed of desired thickness, another cell type could be injected to seed another layer. (Step 410). For example, additional and different cell types may be deposited on top of the first layer in order to produce an extracellular matrix and develop structural integrity. After the completion of the culture, the bioreactor 102 is opened and the mandrel 106 is removed from the bioreactor 102. (Step 412). The tissue construct is then slipped off the mandrel 106. (Step 414). A reverse pressure gradient may be applied to ease the process of removing the tissue construct from the mandrel 106. If further assistance is required to remove the construct from the mandrel 106, a brief collagenase infusion may be applied on the luminal side of the mandrel 106 in addition to applying a reverse pressure gradient to loosen the construct.

Once the tissue construct is separated from the mandrel 106, the lumen of the construct may be endothelialized by the CFTA process. (Step 416). The endothelialization process is similar to the process described for forming the tissue construct, except that the direction of flow of the culture media in the system is reversed. First the tissue construct, which has preferably been removed from the mandrel 106, is inserted back into the bioreactor and positive pressure is applied inside the tissue construct. (Step 418). As a result, there is a flow of culture media flows into the lumen of the tissue construct, through the tissue construct wall due to the pressure gradient, and then out into the bioreactor 102. Next, a clamp 128 on an outlet 112 is closed. With the clamp 128 closed, endothelial cells are injected into the bioreactor 102 via one or more of the outlets 112. (Step 420). The endothelial cells are then allowed to seed on the inside/lumen of the construct via the CFTA process. (Step 420). Positive pressure may be maintained for 12 to 24 hours, and additional cells may optionally be injected into the bioreactor 102. (Step 422). After the endothelialization process, the tissue construct is again removed from the bioreactor 102. (See Step 424).

If endothelialization is not required but instead a sheet of tissue is desired, the tissue construct may be cut open to form a sheet of tissue. (Steps 426 and 428).

The present invention provides for constructs of uniform thickness. Uniformity of cell seeding on the mandrel 106 is assured by a uniform, symmetric pressure-driven flow field that is self-correcting. Specifically, any irregularity in the cell seeding process will locally alter the hydraulic resistance of the mandrel 106 at that location on the mandrel 106, which in turn will result in an inverse effect on the fluid flow and the fluid drag that drives the cell deposition. Thus, local over-deposition will locally increase the hydraulic resistance at that location and will serve to divert fluid flow, thereby increasing the deposition of cells on the rest of the mandrel 106. This self-correcting characteristic assures uniformity in construct thickness. Uneven distribution of cells in suspension caused by sedimentation prior to deposition may be addressed by stirring at the base of the bioreactor 102.

The processes of the present invention are not limited to the assembly or formation of any one particular tissue or organ. Rather, the present invention provides for general in vitro tissue assembly methodologies and is well suited to engineering a wide array of tissues and organs, including but not limited to multilayered vascularized organs or tissues. Possible applications include, for example, assembly of cylindrical or sheet tissues, such as, e.g., TEVGs, tissue engineered esophagus, tissue engineered trachea, tissue engineered skin, tissue engineered muscle (both skeletal and cardiac), tissue engineered liver, and the like.

Different suspensions of cells may be seeded in order to form different types of tissues. When using different suspensions, each different suspension of cells is infused sequentially into the bioreactor. For example, to form endothelialized TEVG constructs, seedings would consist of smooth muscle cells, followed by fibroblasts. Other cell combinations that could be used for seedings include: for tissue engineered esophagus, epithelial cells followed by smooth muscle cells or mesenchymal stem cells; for tissue engineered trachea, chondrocytes followed by fibroblasts or mesenchymal stem cells; for tissue engineered skin, fibroblasts followed by keratynocytes; for tissue engineered muscle, skeletal or cardiac muscle cells; for tissue engineered liver, endothelial cells followed by hepatocytes.

The present invention may be used to produce TEVGs in a three-stage process, which will be described with reference to the production of smooth muscle tissue. Using the processes described herein, smooth muscle cell tissue constructs are assembled in tubular form on the mandrel. Next, fibroblasts are seeded on the outside of the smooth muscle cell layer, which will act as the media, again by the convective flow, thereby forming the adventitia. At this point, the mandrel will be removed from the bioreactor and endothelial cells will be seeded and allowed to attach on the luminal smooth muscle cell surface of the TEVG by a reverse flow, yielding an intima layer. In several respects, this process will mimic the mechanical environment of native arteries. It is known that smooth muscle cells are subjected to physiologically significant shear stress (~1 dyne/cm$^2$) in native arteries, induced by transmural pressure gradients and that this shear stress can be estimated as follows:

$$\tau = B \frac{\mu v}{\sqrt{k}}$$

where B is the Brinkman number and is approximately equal to one. Furthermore, these shear stresses induce prostaglandin synthesis in smooth muscle cells and may be involved in vessel wall homeostasis. With the present invention, the porosity of the mandrel has a similar effect as the fenestral pores of the inner elastic lamina, which increase local shear stress on the smooth muscle cells and further promote homeostasis. Current research has convincingly shown that the fluid mechanical environment involved in the production of the TEVG is very important, particularly in terms of maintaining differentiation and ECM production. The present invention provides the first tissue assembly methodology that utilizes fluid shear stress as a means of promoting tissue growth and proper development.

In vivo biocompatibility in the clinical setting may be enhanced if the TEVG is composed of autologous cells. For example, since the methods of the present invention do not solely rely on proliferation; the present invention is readily adaptable to the use of adult cells derived from a patient awaiting CABG surgery. The fibroblasts may be derived from a skin biopsy, while the endothelial cells and smooth muscle cells may be derived from a native vessel with minimal donor site morbidity, such as, e.g., an external jugular vein. Alternatively, smooth muscle cells can be cultured from autologous adipose-derived stem cells, while endothelial cells may be harvested similarly from autologous circulating endothelial precursor cells.

Studies using the present invention have been conducted with DSF-3 dog skin fibroblasts. A prototype bioreactor was built, and a porous (20 μm pores), 3 inch polyethylene mandrel was used. Flow conditions were examined by injecting dye. Deposition uniformity was examined by injecting collagen microcarrier beads. Cryopreserved DSF-3s were expanded in standard DSF-3 culture (20% FBS, 2% L-glutamine, 1% P/S). One confluent 75 cm$^2$ tissue culture flask was then scraped and the resulting fibroblast clumps were injected into the bioreactor and deposited on the mandrel, via fluid flow generated by a 1 psi transmural pressure gradient across the mandrel wall. The entire flow system was placed in a 37° C. water bath and connected to a 5% $CO_2$/95% $O_2$ gas flow system. A peristaltic pump was used to maintain convective flow conditions, subjecting cells to a 1 psi transmural pressure difference, which yielded physiological flow conditions of approximately 1 dyne/cm$^2$ transmural shear stress. Culture media was refreshed every three days and additional seedings of trypsinized fibroblasts were done every six days. Total culture duration was either seven or fourteen days. At the end of culture, the mandrel was extracted and stained with Ponceau Red protein stain, allowing the visualization of the formed tissue.

Dye studies revealed uniform flow conditions. Collagen microcarrier bead studies revealed complete coverage of the mandrel, uniform in both the axial and circumferential directions. Fibroblast culture experiments revealed a minimal, but uniform tissue film after one week of culture, with one seeding and an approximately 1 mm thick tissue construct after two weeks of culture and two cell seedings. In this case, the pump pressure setting had to be gradually increased to 2.1 psi to maintain the desired 1 psi transmural pressure gradient and 1 dyne/cm$^2$ shear stress for the thin tissue layers. Once removed from the bioreactor and stained, scraping the tissue construct with tweezers resulted in the tissue layer readily pealing off and revealing a clean mandrel beneath.

Though the invention has been described with respect to specific preferred embodiments, many variations and modifications will become apparent to those skilled in the art. It is therefore intended and expected that the appended claims be interpreted as broadly as possible in view of the prior art in order to include all such variations and modifications.

What is claimed is:

1. A method for making an engineered tissue construct, comprising the steps of:
   providing a chamber comprising an interior volume, at least one inlet, and at least one outlet;
   providing a mandrel comprising a porous surface that defines an interior volume, the mandrel being disposed within the chamber, the interior volume of the mandrel communicating with the at least one outlet;
   infusing culture media through the at least one inlet into the interior volume of the chamber;
   infusing a suspension of cells into the interior volume of the chamber;
   aspirating culture media from the at least one outlet, wherein culture media passes from the interior volume of the chamber through the pores of the mandrel to the interior volume of the mandrel, and cells are deposited on the surface of the mandrel;
   removing the mandrel from the chamber after a tissue construct is formed on the mandrel;
   removing the tissue construct from the mandrel;
   inserting the tissue construct into the chamber;
   reversing the flow of culture media within the interior volume of the chamber; and
   infusing endothelial cells into the interior volume of the chamber, wherein the endothelial cells pass into the tissue construct and are deposited on an inner surface of the tissue construct.

2. The method of claim 1, wherein the cells deposited on the surface of the mandrel are maintained so that the cells secrete extracellular matrix and form a tissue.

3. The method of claim 2, wherein the tissue is formed in the shape of the mandrel.

4. The method of claim 1, wherein the steps of aspirating culture media from the at least one outlet and infusing culture media through the at least one inlet are continued until a continuous cellular membrane is formed around the mandrel.

5. The method of claim 4, wherein the mandrel is a elongate tubular member having a first end, a second end, and a lumen therebetween, the lumen being in fluid communication with the at least one outlet, and wherein a cellular membrane is formed around the mandrel in the shape of a vessel.

6. The method of claim 4, wherein the suspension of cells is a first suspension of cells, the method further comprising infusing a second suspension of cells of a different cell type from the first suspension of cells into the culture media to form a layered tissue construct.

7. The method of claim 6, wherein the first suspension of cells comprises smooth muscle cells and the second suspension of cells comprises fibroblasts.

8. The method of claim 6, wherein the first suspension of cells comprises epithelia cells and the second suspension of cells comprises smooth muscle cells.

9. The method of claim 6, wherein the first suspension of cells comprises chondrocytes and the second suspension of cells comprises fibroblasts.

10. The method of claim 6, wherein the first suspension of cells comprises fibroblasts and the second suspension of cells comprises keratynocytes.

11. The method of claim 6, wherein the first suspension of cells comprises endothelial cells and the second suspension of cells comprises hepatocytes.

12. The method of claim 1, wherein the suspension of cells comprises skeletal muscle cells.

13. The method of claim 1, wherein the suspension of cells comprises cardiac muscle cells.

14. A method for making an engineered tissue construct, comprising the steps of:
   infusing a culture media into an interior volume of a chamber comprising the interior volume, an inlet, and an outlet;
   infusing a suspension of cells into the interior volume of the chamber;
   aspirating culture media from the interior volume, wherein a mandrel having an interior volume and a surface with a plurality of pores is located within the interior volume of the chamber, and culture media passes from the interior volume of the chamber through the pores of the mandrel to the interior volume of the mandrel and the cells are deposited on the surface of the mandrel; and removing from the mandrel a tissue construct formed by the cells deposited on the surface of the mandrel by applying a reverse pressure gradient to the mandrel.

15. The method of claim 14, wherein infusing a suspension of cells comprises:

infusing a plurality of suspensions of cells into the interior volume of the chamber, each suspension of cells comprising a distinct cell type.

16. The method of claim 15, wherein each suspension of cells is infused sequentially into the interior volume of the chamber.

17. A method for making an engineered tissue construct, comprising the steps of:

infusing a culture media into an interior volume of a chamber comprising the interior volume, an inlet, and an outlet;

infusing a suspension of cells into the interior volume of the chamber;

aspirating culture media from the interior volume, wherein a mandrel having an interior volume and a surface with a plurality of pores is located within the interior volume of the chamber, and culture media passes from the interior volume of the chamber through the pores of the mandrel to the interior volume of the mandrel and the cells are deposited on the surface of the mandrel; and removing from the mandrel a tissue construct formed by the cells deposited on the surface of the mandrel by applying a collagenase infusion on the mandrel.

18. A method for making an engineered tissue construct, comprising the steps of:

infusing a culture media into an interior volume of a chamber comprising the interior volume, an inlet, and an outlet;

infusing a suspension of cells into the interior volume of the chamber;

aspirating culture media from the interior volume, wherein a mandrel having an interior volume and a surface with a plurality of pores is located within the interior volume of the chamber, and culture media passes from the interior volume of the chamber through the pores of the mandrel to the interior volume of the mandrel and the cells are deposited on the surface of the mandrel;

removing the mandrel from the chamber after a tissue construct is formed on the mandrel;

removing the tissue construct from the mandrel;

inserting the tissue construct into the chamber;

reversing the flow of culture media within the interior volume of the chamber; and infusing endothelial cells into the interior volume of the chamber, wherein the endothelial cells pass into tissue construct and are deposited on an inner surface of the tissue construct.

* * * * *